United States Patent
Wu et al.

(10) Patent No.: US 10,760,067 B2
(45) Date of Patent: Sep. 1, 2020

(54) β-GALACTOSIDASE MUTANT, AND PREPARATION METHOD AND APPLICATION THEREOF

(71) Applicant: Jiangnan University, Wuxi (CN)

(72) Inventors: Jing Wu, Wuxi (CN); Dan Wu, Wuxi (CN); Xin Gao, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 16/044,591

(22) Filed: Jul. 25, 2018

(65) Prior Publication Data

US 2019/0218536 A1    Jul. 18, 2019

(30) Foreign Application Priority Data

Jan. 15, 2018   (CN) .......................... 2018 1 0033883

(51) Int. Cl.
| | |
|---|---|
| *C12N 9/38* | (2006.01) |
| *C12N 15/66* | (2006.01) |
| *C12N 15/00* | (2006.01) |
| *A23L 33/21* | (2016.01) |
| *A23C 9/12* | (2006.01) |
| *C12N 15/81* | (2006.01) |

(52) U.S. Cl.
CPC ............ *C12N 9/2471* (2013.01); *A23L 33/21* (2016.08); *C12Y 302/01023* (2013.01); *A23C 9/1206* (2013.01); *C12N 15/66* (2013.01); *C12N 15/81* (2013.01)

(58) Field of Classification Search
CPC ............ C12Y 302/01023; C12P 19/04; C12N 9/2471; C12N 9/2468; C12N 15/80
USPC .......................... 435/101, 207, 257.2; 514/54
See application file for complete search history.

(56) References Cited

PUBLICATIONS

Davos et al., Proteins: Structure, Function and Genetics, 2000, vol. 41: 98-107.*
Wristlock et al., Quarterly Reviews of Biophysics 2003, vol. 36 (3): 307-340.*
Kwiatkowski et al., Biochemistry 38:11643-11650, 1999.*
Kisselev L., Structure, 2002, vol. 10: 8-9.*

* cited by examiner

*Primary Examiner* — Robert B Mondesi
*Assistant Examiner* — Mohammad Y Meah
(74) *Attorney, Agent, or Firm* — IPro, PLLC (57) ABSTRACT

The present invention discloses a β-galactosidase mutant, and a preparation method and application thereof, belonging to the fields of gene engineering and enzyme engineering. Amino acids of specific sites in the β-galactosidase are mutated, the β-galactosidase is transferred into a recombinant bacterium, and enzymatic transformation is performed under optimized conditions, so that the yield of galactooligosaccharide produced by the mutant reaches 59.8%, which is increased by about 70% as compared with that of wild enzyme, thereby implementing the increase of the galactooligosaccharide yield. The present invention has very high industrialized application value.

6 Claims, 1 Drawing Sheet

Specification includes a Sequence Listing.

SEQUENCE LISTING

<160> NUMBER OF SEQ ID NOS: 12

<210> SEQ ID NO 1
<211> LENGTH: 3018
<212> TYPE: DNA
<213> ORGANISM: Artificial Sequence
<220> FEATURE:
<223> OTHER INFORMATION: Synthetic DNA

<400> SEQUENCE: 1

```
atgaagctcc tctctgttgc tgctgttgcc ttgctggcgg cacaggcagc gggtgcttcc      60
atcaagcatc gtctcaatgg cttcacgatc ctggaacatc cggatccggc gaaaagagac     120
ttgctgcaag acattgttac atgggatgac aaatctctgt tcatcaatgg agagaggatt     180
atgttattca gcggagaagt gcatcctttc agattgccag taccttcgct ttggcttgat     240
atcttccaca agatcagggc tcttggtttc aactgtgtat cttcctatat tgattgggct     300
cttctggagg aaaagcctgg cgactacaga gcagaaggca tctttgctct ggaacccttc     360
tttgatgcag ccaaggaagc aggcatttat ctgatcgccc gccccggttc gtacatcaat     420
gccgaggtct caggcggtgg cttccctgga tggttgcaga gggtcaatgg cactcttcgc     480
tcgtctgatg agccattcct taaagctact gataactata tcgccaatgc cgctgctgcc     540
gtggcgaagg ctcaaatcac gaatggaggg ccagtaattc tctaccagcc cgaaaacgaa     600
tacagcggtg gctgctgcgg tgtcaaatac cccgatgcag actacatgca gtatgttatg     660
gatcaggccc ggaaggctga cattgttgta cctttcatca gcaacgatgc ctcaccttct     720
gggcacaatg ctcctggaag tggaacgggc gctgttgata tttatggtca cgatagctat     780 ccctcggct ttgattgcgc aaacccatcc gtatggcccg agggtaaact gcccgacaac     840
ttccgcacgc tccatcttga gcagagccca tcaactccgt attcacttct tgagttccaa     900
gcgggtgctt tcgacccatg gggtggaccc ggctttgaaa aatgctatgc cctcgttaac     960
cacgaattct cgagagtttt ctataggaac gacttgagtt tcggagtttc tacctttaac    1020
ttatacatga ctttcggcgg aacaaactgg ggtaacctcg gacatcccgg tggatataca    1080
tcctacgact acggatcgcc tataactgaa acgcgaaacg ttacacggga gaagtacagc    1140
gacataaagc tccttgccaa cttttgtcaaa gcatcgccat cctatctcac cgctactccc    1200
agaaacctga ctactggtgt ttacacagac acatctgacc tggctgtcac cccgttaatt    1260
ggtgatagtc caggctcatt cttcgtggtc agacatacgg actattccag ccaagagtca    1320
acctcgtaca aacttaagct tcctaccagt gctggtaacc tgactattcc ccagctggag    1380
ggcactctaa gtctcaacgg acgtgactca aaaattcatg ttgttgatta taatgtgtct    1440
ggaacgaaca ttatctattc gacagctgaa gtcttcacct ggaagaagtt tgacggtaac    1500
aaggtcctgg tgttatacgg cggaccgaag gaacaccatg aattggccat gcctccaag     1560 tcaaatgtga ccatcatcga aggttcggac tctggaattg tctcaacgag aagggcagc     1620 tctgttatca ttggctggga tgtctcttct actcgtcgca tcgttcaagt cggtgacttg    1680
agagtgttcc tgcttgatag gaactctgct tacaactact gggtccccga actccccaca    1740
gaaggtactt ctcccgggtt cagcacttcg aagacgaccg cctcctccat tatgtgaag     1800
```

```
gctggctacc tcctccgagg cgctcacctt gatggtgctg atcttcatct tactgctgat    1860
ttcaatgcca ccaccccgat tgaagtgatc ggtgctccaa caggcgctaa gaatctgttc    1920
gtgaatggtg aaaaggctag ccacacagtc gacaagaacg gcatctggag cagtgaggtc    1980
aagtacgcgg ctccagagat caagctcccc ggtttgaagg atttggactg gaagtatctg    2040
gacacgcttc ccgaaattaa gtcttcctat gatgactcgg cctgggtttc ggcagacctt    2100
ccaaagacaa agaacactca ccgtcctctt gacacaccaa catcgctata ctcctctgac    2160
tatggcttcc acactggcta cctgatctac agggtcact tcgttgccaa cggcaaggaa     2220
agcgaatttt ttattcgcac acaaggcggt agcgcattcg aagttccgt atggctgaac     2280 gagacgtatc tgggctcttg gactggtgcc gattatgcga tggacggtaa ctctacctac    2340
aagctatctc agctggagtc gggcaagaat tacgtcatca ctgtggttat tgataacctg    2400
ggtctcgacg agaattggac ggtcggcgag gaaaccatga agaatcctcg tggtattctt    2460
agctacaagc tgagcggaca agacgccagc gcaatcacct ggaagctcac tggtaacctc    2520
ggaggagaag actaccagga taaggttaga ggacctctca acgaaggtgg actgtacgca    2580
gagcgccagg gcttccatca gcctcagcct ccaagcgaat cctgggagtc gggcagtccc    2640
cttgaaggcc tgtcgaagcc gggtatcgga ttctacactg cccagttcga ccttgacctc    2700
ccgaagggct gggatgtgcc gctgtacttc aactttggca acaacaccca ggcggctcgg    2760
gcccagctct acgtcaacgg ttaccagtat ggcaagttca ctggaaacgt tgggccacag    2820
accagcttcc ctgttcccga aggtatcctg aactaccgcg gaaccaacta tgtggcactg    2880
agtctttggg cattggagtc ggacggtgct aagctgggta gcttcgaact gtcctacacc    2940
accccagtgc tgaccggata cgggaatgtt gagtcacctg agcagcccaa gtatgagcag    3000
cggaagggag catactaa                                                  3018
```

<210> SEQ ID NO 2
<211> LENGTH: 1005
<212> TYPE: PRT
<213> ORGANISM: Artificial Sequence
<220> FEATURE:
<223> OTHER INFORMATION: Protein translated from synthetic DNA

<400> SEQUENCE: 2

```
Met Lys Leu Leu Ser Val Ala Ala Val Ala Leu Leu Ala Ala Gln Ala
1               5                   10                  15

Ala Gly Ala Ser Ile Lys His Arg Leu Asn Gly Phe Thr Ile Leu Glu
            20                  25                  30

His Pro Asp Pro Ala Lys Arg Asp Leu Leu Gln Asp Ile Val Thr Trp
        35                  40                  45

Asp Asp Lys Ser Leu Phe Ile Asn Gly Glu Arg Ile Met Leu Phe Ser
    50                  55                  60

Gly Glu Val His Pro Phe Arg Leu Pro Val Pro Ser Leu Trp Leu Asp
65                  70                  75                  80

Ile Phe His Lys Ile Arg Ala Leu Gly Phe Asn Cys Val Ser Phe Tyr
                85                  90                  95

Ile Asp Trp Ala Leu Leu Glu Gly Lys Pro Gly Asp Tyr Arg Ala Glu
            100                 105                 110

Gly Ile Phe Ala Leu Glu Pro Phe Phe Asp Ala Ala Lys Glu Ala Gly
        115                 120                 125

Ile Tyr Leu Ile Ala Arg Pro Gly Ser Tyr Ile Asn Ala Glu Val Ser
    130                 135                 140
```

```
Gly Gly Gly Phe Pro Gly Trp Leu Gln Arg Val Asn Gly Thr Leu Arg
145                 150                 155                 160
Ser Ser Asp Glu Pro Phe Leu Lys Ala Thr Asp Asn Tyr Ile Ala Asn
            165                 170                 175
Ala Ala Ala Ala Val Ala Lys Ala Gln Ile Thr Asn Gly Gly Pro Val
                180                 185                 190
Ile Leu Tyr Gln Pro Glu Asn Glu Tyr Ser Gly Gly Cys Cys Gly Val
        195                 200                 205
Lys Tyr Pro Asp Ala Asp Tyr Met Gln Tyr Val Met Asp Gln Ala Arg
210                 215                 220
Lys Ala Asp Ile Val Val Pro Phe Ile Ser Asn Asp Ala Ser Pro Ser
225                 230                 235                 240
Gly His Asn Ala Pro Gly Ser Gly Thr Gly Ala Val Asp Ile Tyr Gly
                245                 250                 255
His Asp Ser Tyr Pro Leu Gly Phe Asp Cys Ala Asn Pro Ser Val Trp
            260                 265                 270
Pro Glu Gly Lys Leu Pro Asp Asn Phe Arg Thr Leu His Leu Glu Gln
        275                 280                 285
Ser Pro Ser Thr Pro Tyr Ser Leu Leu Glu Phe Gln Ala Gly Ala Phe
290                 295                 300
Asp Pro Trp Gly Gly Pro Gly Phe Glu Lys Cys Tyr Ala Leu Val Asn
305                 310                 315                 320
His Glu Phe Ser Arg Val Phe Tyr Arg Asn Asp Leu Ser Phe Gly Val
                325                 330                 335
Ser Thr Phe Asn Leu Tyr Met Thr Phe Gly Gly Thr Asn Trp Gly Asn
            340                 345                 350
Leu Gly His Pro Gly Gly Tyr Thr Ser Tyr Asp Tyr Gly Ser Pro Ile
        355                 360                 365
Thr Glu Thr Arg Asn Val Thr Arg Glu Lys Tyr Ser Asp Ile Lys Leu
370                 375                 380
Leu Ala Asn Phe Val Lys Ala Ser Pro Ser Tyr Leu Thr Ala Thr Pro
385                 390                 395                 400
Arg Asn Leu Thr Thr Gly Val Tyr Thr Asp Thr Ser Asp Leu Ala Val
                405                 410                 415
Thr Pro Leu Ile Gly Asp Ser Pro Gly Ser Phe Phe Val Val Arg His
            420                 425                 430
Thr Asp Tyr Ser Ser Gln Glu Ser Thr Ser Tyr Lys Leu Lys Leu Pro
        435                 440                 445
Thr Ser Ala Gly Asn Leu Thr Ile Pro Gln Leu Glu Gly Thr Leu Ser
450                 455                 460
Leu Asn Gly Arg Asp Ser Lys Ile His Val Val Asp Tyr Asn Val Ser
465                 470                 475                 480
Gly Thr Asn Ile Ile Tyr Ser Thr Ala Glu Val Phe Thr Trp Lys Lys
                485                 490                 495
Phe Asp Gly Asn Lys Val Leu Val Leu Tyr Gly Gly Pro Lys Glu His
            500                 505                 510
His Glu Leu Ala Ile Ala Ser Lys Ser Asn Val Thr Ile Ile Glu Gly
        515                 520                 525
Ser Asp Ser Gly Ile Val Ser Thr Arg Lys Gly Ser Ser Val Ile Ile
530                 535                 540
Gly Trp Asp Val Ser Ser Thr Arg Arg Ile Val Gln Val Gly Asp Leu
545                 550                 555                 560
Arg Val Phe Leu Leu Asp Arg Asn Ser Ala Tyr Asn Tyr Trp Val Pro
```

```
                    565                 570                 575
Glu Leu Pro Thr Glu Gly Thr Ser Pro Gly Phe Ser Thr Ser Lys Thr
                580                 585                 590
Thr Ala Ser Ser Ile Ile Val Lys Ala Gly Tyr Leu Leu Arg Gly Ala
                595                 600                 605
His Leu Asp Gly Ala Asp Leu His Leu Thr Ala Asp Phe Asn Ala Thr
            610                 615                 620
Thr Pro Ile Glu Val Ile Gly Ala Pro Thr Gly Ala Lys Asn Leu Phe
625                 630                 635                 640
Val Asn Gly Glu Lys Ala Ser His Thr Val Asp Lys Asn Gly Ile Trp
                645                 650                 655
Ser Ser Glu Val Lys Tyr Ala Ala Pro Glu Ile Lys Leu Pro Gly Leu
                660                 665                 670
Lys Asp Leu Asp Trp Lys Tyr Leu Asp Thr Leu Pro Glu Ile Lys Ser
                675                 680                 685
Ser Tyr Asp Asp Ser Ala Trp Val Ser Asp Leu Pro Lys Thr Lys
            690                 695                 700
Asn Thr His Arg Pro Leu Asp Thr Pro Thr Ser Leu Tyr Ser Ser Asp
705                 710                 715                 720
Tyr Gly Phe His Thr Gly Tyr Leu Ile Tyr Arg Gly His Phe Val Ala
                725                 730                 735
Asn Gly Lys Glu Ser Glu Phe Phe Ile Arg Thr Gln Gly Gly Ser Ala
                740                 745                 750
Phe Gly Ser Ser Val Trp Leu Asn Glu Thr Tyr Leu Gly Ser Trp Thr
                755                 760                 765
Gly Ala Asp Tyr Ala Met Asp Gly Asn Ser Thr Tyr Lys Leu Ser Gln
            770                 775                 780
Leu Glu Ser Gly Lys Asn Tyr Val Ile Thr Val Ile Asp Asn Leu
785                 790                 795                 800
Gly Leu Asp Glu Asn Trp Thr Val Gly Glu Glu Thr Met Lys Asn Pro
                805                 810                 815
Arg Gly Ile Leu Ser Tyr Lys Leu Ser Gly Gln Asp Ala Ser Ala Ile
                820                 825                 830
Thr Trp Lys Leu Thr Gly Asn Leu Gly Gly Glu Asp Tyr Gln Asp Lys
            835                 840                 845
Val Arg Gly Pro Leu Asn Glu Gly Gly Leu Tyr Ala Glu Arg Gln Gly
            850                 855                 860
Phe His Gln Pro Gln Pro Pro Ser Glu Ser Trp Glu Ser Gly Ser Pro
865                 870                 875                 880
Leu Glu Gly Leu Ser Lys Pro Gly Ile Gly Phe Tyr Thr Ala Gln Phe
                885                 890                 895
Asp Leu Asp Leu Pro Lys Gly Trp Asp Val Pro Leu Tyr Phe Asn Phe
            900                 905                 910
Gly Asn Asn Thr Gln Ala Ala Arg Ala Gln Leu Tyr Val Asn Gly Tyr
            915                 920                 925
Gln Tyr Gly Lys Phe Thr Gly Asn Val Gly Pro Gln Thr Ser Phe Pro
            930                 935                 940
Val Pro Glu Gly Ile Leu Asn Tyr Arg Gly Thr Asn Tyr Val Ala Leu
945                 950                 955                 960
Ser Leu Trp Ala Leu Glu Ser Asp Gly Ala Lys Leu Gly Ser Phe Glu
                965                 970                 975
Leu Ser Tyr Thr Thr Pro Val Leu Thr Gly Tyr Gly Asn Val Glu Ser
            980                 985                 990
```

Pro Glu Gln Pro Lys Tyr Glu Gln Arg Lys Gly Ala Tyr
            995                 1000                1005

<210> SEQ ID NO 3
<211> LENGTH: 29
<212> TYPE: DNA
<213> ORGANISM: Artificial Sequence
<220> FEATURE:
<223> OTHER INFORMATION: Synthetic DNA

<400> SEQUENCE: 3
tccacaagat cagggctctt ggtttcaac                             29

<210> SEQ ID NO 4
<211> LENGTH: 29
<212> TYPE: DNA
<213> ORGANISM: Artificial Sequence
<220> FEATURE:
<223> OTHER INFORMATION: Synthetic DNA

<400> SEQUENCE: 4
gttgaaacca agagccctga tcttgtgga                             29

<210> SEQ ID NO 5
<211> LENGTH: 29
<212> TYPE: DNA
<213> ORGANISM: Artificial Sequence
<220> FEATURE:
<223> OTHER INFORMATION: Synthetic DNA

<400> SEQUENCE: 5
ccggttcgta catctgtgcc gaggtctca                             29

<210> SEQ ID NO 6
<211> LENGTH: 29
<212> TYPE: DNA
<213> ORGANISM: Artificial Sequence
<220> FEATURE:
<223> OTHER INFORMATION: Synthetic DNA

<400> SEQUENCE: 6
tgagacctcg gcacagatgt acgaaccgg                             29

<210> SEQ ID NO 7
<211> LENGTH: 29
<212> TYPE: DNA
<213> ORGANISM: Artificial Sequence
<220> FEATURE:
<223> OTHER INFORMATION: Synthetic DNA

<400> SEQUENCE: 7
ctcgacgaga atttcacggt cggcgagga                             29

<210> SEQ ID NO 8
<211> LENGTH: 29
<212> TYPE: DNA
<213> ORGANISM: Artificial Sequence
<220> FEATURE:
<223> OTHER INFORMATION: Synthetic DNA

<400> SEQUENCE: 8
tcctcgccga ccgtgaaatt ctcgtcgag                             29

<210> SEQ ID NO 9
<211> LENGTH: 34

```
<212> TYPE: DNA
<213> ORGANISM: Artificial Sequence
<220> FEATURE:
<223> OTHER INFORMATION: Synthetic DNA

<400> SEQUENCE: 9
agctatcccc tcggctggga ttgcgcaaac ccat                                34

<210> SEQ ID NO 10
<211> LENGTH: 34
<212> TYPE: DNA
<213> ORGANISM: Artificial Sequence
<220> FEATURE:
<223> OTHER INFORMATION: Synthetic DNA

<400> SEQUENCE: 10
atgggtttgc gcaatcccag ccgaggggat agct                                34

<210> SEQ ID NO 11
<211> LENGTH: 30
<212> TYPE: DNA
<213> ORGANISM: Artificial Sequence
<220> FEATURE:
<223> OTHER INFORMATION: Synthetic DNA

<400> SEQUENCE: 11
tccaagcggg tgctaatgac ccatggggtg                                      30

<210> SEQ ID NO 12
<211> LENGTH: 30
<212> TYPE: DNA
<213> ORGANISM: artificial sequence
<220> FEATURE:
<223> OTHER INFORMATION: Synthetic DNA

<400> SEQUENCE: 12
caccccatgg gtcattagca cccgcttgga                                      30
```

β-GALACTOSIDASE MUTANT, AND PREPARATION METHOD AND APPLICATION THEREOF

TECHNICAL FIELD

The present invention relates to a β-galactosidase mutant, and a preparation method and application thereof, belonging to the fields of gene engineering and enzyme engineering.

BACKGROUND

Galactooligosaccharide (GOS) is a functional oligosaccharide that is currently widely used in the food industry. As a new functional food additive, the GOS has attracted worldwide attention because of its unique physiological functions and excellent physicochemical properties. With the continuous advancing of development and research of GOS, coupled with abundant raw materials in China and the unlimited potential of the consumer market, the production of GOS has already set off a strong momentum all over the country. At present, the production of oligosaccharides in China is still an emerging industry. The development of GOS has not yet reached its scale. The main reason for restricting the production of GOS in China is the lack of industrial enzymes with excellent performance. Therefore, it is very important to find industrial enzymes with excellent performance.

β-galactosidase is a main enzyme used in industrial enzymatic method production of galactooligosaccharide. β-galactosidase derived from different microorganisms has different ability to generate GOS due to different properties. Currently known better GOS-producing strains are *B. circulans, Kluyveromyces Lactis* and *A. oryzae*. Although the yield of *B. circulans* (*Bacillus circulans*) is higher (48.3%), its product of GOS production is mainly 4'GalLac which has a poor probiotic effect. A main product of GOS produced by *A. oryzae* as a food-safe strain is 6'GalLac. 6'GalLac has a better probiotic effect than 4'GalLac, but its yield is only about 19%, which greatly limits its application.

Therefore, improving the yield of *Aspergillus oryzae* derived β-galactosidase for producing GOS to create conditions for its industrial production is a technical problem to be solved at present.

SUMMARY

The present invention firstly aims to provide a β-galactosidase mutant, wherein the mutant results from mutation of one or more amino acid sites of β-galactosidase of which an amino acid sequence is as shown in SEQ ID NO.2.

In an implementation of the present invention, the mutant results from mutation of one or more sites at the 140th, 264th, 304th and 806th positions of the β-galactosidase of which an amino acid sequence is as shown in SEQ ID NO.2.

In an implementation of the present invention, the mutant results from mutation of asparagine (Asn) at the 140th position of the β-galactosidase of which the amino acid sequence is as shown in SEQ ID NO.2 to cysteine (Cys), wherein the mutant is named N140C.

In an implementation of the present invention, the mutant results from mutation of phenylalanine (Phe) at the 264th position of the β-galactosidase of which the amino acid sequence is as shown in SEQ ID NO.2 to tryptophan (Trp), wherein the mutant is named F264W.

In an implementation of the present invention, the mutant results from mutation of phenylalanine (Phe) at the 304th position of the β-galactosidase of which the amino acid sequence is as shown in SEQ ID NO.2 to glutamine (Gln), wherein the mutant is named F304Q.

In an implementation of the present invention, the mutant results from mutation of tryptophan (Trp) at the 806th position of the β-galactosidase of which the amino acid sequence is as shown in SEQ ID NO.2 to phenylalanine (Phe), wherein the mutant is named W806F.

In an implementation of the present invention, the mutant results from mutation of phenylalanine (Phe) at the 264th position of the β-galactosidase of which the amino acid sequence is as shown in SEQ ID NO.2 to tryptophan (Trp) and asparagine (Asn) at the 140th position to cysteine (Cys), wherein the mutant is named N140C/F264W.

In an implementation of the present invention, the mutant results from mutation of asparagine (Asn) at the 140th position of the β-galactosidase of which the amino acid sequence is as shown in SEQ ID NO.2 to cysteine (Cys) and tryptophan (Trp) at the 806th position to phenylalanine (Phe), wherein the mutant is named N140C/W806F.

The present invention secondly aims to provide a preparation method of the β-galactosidase mutant, which specifically comprises the following steps:

(1) according to determined mutant sites, designing mutagenic primers of site-directed mutagenesis, and performing site-directed mutagenesis by using a vector carrying the β-galactosidase gene as a template; and constructing a plasmid vector containing the gene coding the mutant;

(2) transforming a mutant plasmid into a host cell; and (3) selecting a positive clone, performing fermentation culture, and performing centrifuging, wherein supernate is a crude enzyme solution of the β-galactosidase mutant.

In an implementation of the present invention, the plasmid vector is any of pET series or pPIC9k.

The present invention thirdly aims to provide a method for preparing galactooligosaccharide by using the β-galactosidase mutant, which specifically comprises the following steps:

(1) by using lactose with concentration of 400 g/L-600 g/L as a substrate, adding the β-galactosidase, and adding an acetic acid-sodium acetate buffer, wherein pH is 4.5-5;

(2) performing enzymatic transformation in a shaking water bath, wherein reaction temperature is 40-60° C.;

(3) performing reaction within 5-36 h, wherein a sample is taken every 4 hours during the reaction; and (4) performing liquid-phase analysis on a reaction product, and calculating yield. In an implementation of the present invention, an addition amount of the β-galactosidase is 2.5-5 U/mL.

The present invention has the following beenficial effects: by constructing the *Aspergillus oryzae* derived β-galactosidase mutant, the maximum GOS yield by transforming lactose is increased from 35.2% of a wild bacterium to 59.8%, so that the problem of lower industrial production yield of this enzyme is solved. Compared with the wild type, this enzyme has higher glucoside transformation activity, and is suitable for industrial production.

When the present invention is applied to galactooligosaccharide (GOS) production, optimum pH for production is 4.5, and optimum temperature is 40° C., which is more suitable for industrial production.

Based on the constructed mutant, the present invention optimizes the production of galactooligosaccharide (GOS) by enzymatic transformation, so that the industrial production value is higher. By performing enzymatic transformation under optimum conditions, the yield reaches 59.8%, which is increased by about 70% as compared with the wild type.

DETAILED DESCRIPTION

BMGY liquid culture medium: YNB: 13.4 g/L; yeast extract: 10 g/L; peptone: 20 g/L; glycerol: 10 g/L; $K_2HPO_4$: 2.29 g/L; $KH_2PO_4$: 11.8 g/L; $(NH_4)_2SO_4$: 10 g/L;

BMMY liquid culture medium: YNB: 13.4 g/L; yeast extract: 10 g/L; peptone: 20 g/L; methanol: 40 g/L; $K_2HPO_4$: 2.29 g/L; $KH_2PO_4$: 11.8 g/L; $(NH_4)_2SO_4$: 10 g/L.

Enzyme Activity Measuring Method:

β-galactosidase activity analysis uses o-nitrophenyl-β-D-galactopyranoside (oNPG) as a substrate.

Prepare 20 mmol/L oNPG, take 100 µL of a properly diluted fermentation solution or enzyme solution and 1800 µL of 0.1 mol/L pH 4.5 sodium acetate buffer, hold at the temperature of 60° C. for 5 min, adding 100 µL of the substrate, hold at the temperature of 60° C. for 10 min, immediately adding 1 mL of 1 mol/L precooled Na2CO3 solution to stop reaction and perform color development, and measure absorbance at 420 nm with a spectrophotometer.

Definition of enzyme activity unit: under the above analysis conditions, the amount of enzyme that catalytically produces 1 µmol of oNP per minute is one activity unit.

Analysis of Galactooligosaccharide (GOS) Yield by HPLC Method

A 60% (W/V) lactose solution is prepared as a substrate, and certain amounts of wild enzyme and double-mutant enzyme solutions are added, so that the final enzyme activity of the wild type enzyme solution is 10 U/mL and the final enzyme activity of the mutant is 2.5 U/mL (the effect of the amount of enzyme added on the production of GOS was previously performed, and the above conditions were respectively the optimum amounts of enzyme added for the mutant and the wild type). The reaction is performed under the optimum temperature and pH conditions, wherein the reaction for the wild type is performed for 10 h (the time of the maximum yield of the wild type in a pre-experiment), and the reaction for the mutant is performed for 5 h (the time of the maximum yield of the mutant in the pre-experiment). The reaction solution is centrifuged at 12000 rpm for 10 min, and supernate is taken, filtered through a 0.22 nm ultrafiltration membrane to remove 20 uL and subjected to HPLC analysis.

In the reaction solution, the amounts of disaccharides, trisaccharides, tetrasaccharides and pentasaccharides in a product are analyzed by HPLC. Chromatographic conditions for measurement are: Agilent 1200 HPLC chromatograph, Agilent automatic sampler, chromatographic column Hi-Plex Na, (300*7.7 mm), and differential detector Agilent G1362A; a mobile phase is pure water, a flow rate is 0.3 mL/min, and column temperature is set at 80° C.

Chromatographic conditions for measuring disaccharides are: Agilent 1200 HPLC chromatograph, Agilent automatic sampler, chromatographic column NH2-50 4E (4.6 mm*250 mm), and differential detector Agilent G1362A; a mobile phase is a 78% (v/v) acetonitrile-water mixed solution, a flow rate is 0.8 mL/min, and column temperature is set at 35° C.

Measuring Method of Galactooligosaccharide Yield:

Yield (%)=(Mass of the galactooligosaccharide in product/Mass of all saccharides in product)×100%

The galactooligosaccharide yield is the sum of transferred disaccharides, transferred trisaccharides and transferred tetrasaccharides.

Example 1

Preparation of Single Mutant and Wild Enzyme

A β-galactosidase gene (SEQ ID NO.1) is connected to pMD19-T simple to obtain an AorE/pMD19-T simple plasmid, and the AorE/pMD19-T simple plasmid used as a template is subjected to mutation by using Sac1m-F and Sac1m-R as primers. An above PCR product is subjected to Dpn1 digestion, and the obtained plasmid is transformed into an *Escherichia coli* competent cell to obtain an AorE-M/pMD19-T simple plasmid.

Sac1m-F: TCCACAAGATC AGGGCTCTTGGTTTCAAC (mutant sites are underlined)

Sac1m-R: GTTGAAACCA AGAGCCCTGA TCTTGTGGA (mutant sites are underlined) Preparation of wild enzyme: Snab1 and Not1 double-enzyme digestion is performed on the AorE-M/pMD19-T simple plasmid and a pPIC9k vector, enzyme digestion products are connected by a T4 ligase, a connection product is transformed into an *Escherichia coli* JM109 competent cell, and bacterium picking is performed to extract a plasmid, wherein the plasmid is named AorE-M/pPIC9k.

1. Preparation of recombinant bacterium *Pichia pastoris*: the AorE-M/pPIC9k plasmid is electrically transformed into a KM71 yeast competent cell, wherein the recombinant bacterium is named AorE-M/pPIC9k-KM71.

2. Preparation of single mutant: primers for N140C, F264W, F304Q and W806F mutations are respectively designed and synthesized, and the β-galactosidase gene is subjected to site-directed mutagenesis.

PCR amplification of site-directed mutant coding gene: by using a rapid PCR technique, PCR is performed by using a vector AorE-M/pMD19-T simple carrying a gene coding wild type maltooligosyl trehalose synthase as a template to respectively obtain mutated plasmids. Mutagenic primers are as follows:

```
140m-F:
CCGGTTCGTACATCTGTGCCGAGGTCTCA
(mutant sites are underlined)

140m-R:
TGAGACCTCGGCACAGATGTACGAACCGG
(mutant sites are underlined)

806m-F:
CTCGACGAGAATTTCACGGTCGGCGAGGA
(mutant sites are underlined)

806m-R:
TCCTCGCCGACCGTGAAATTCTCGTCGAG
(mutant sites are underlined)

264m-F:
AGCTATCCCCTCGGCTGGGATTGCGCAAACCCAT
(mutant sites are underlined)
```

-continued

264m-R:
ATGGGTTTGCGCAATC<u>CC</u>AGCCGAGGGGATAGCT
(mutant sites are underlined)

F304-Q:
TCCAAGCGGGTGCT<u>AA</u>TGACCCATGGGGTG
(mutant sites are underlined)

264m-R:
CACCCCATGGGTC<u>AT</u>TAGCACCCGCTTGGA
(mutant sites are underlined)

Sequencing is respectively performed to confirm whether the coding gene of the β-galactosidase mutant is correct; Snab1 and Not1 double-enzyme digestion is performed on the plasmid carrying the mutant gene and the pPIC9k vector, enzyme digestion products are connected by a T4 ligase, a connection product is transformed into an *Escherichia coli* JM109 competent cell, bacterium picking is performed to extract the plasmid, and the plasmid is transformed into a yeast KM71 cell to obtain recombinant bacteria AorE-M/pPIC9k-N140C, AorE-M/pPIC9k-F264W, AorE-M/pPIC9k-F3040 and AorE-M/pPIC9k-W806F capable of expressing the mutant gene.

Example 2

Construction of Double Mutants

By using the plasmid of the mutant N140C constructed by the Example 1 as a template for double mutations, according to the primers of site-directed mutagenesis designed by the Example 1, site-directed mutagenesis is performed on the plasmid carrying the gene coding the mutant N140C by a rapid PCR technique to construct double mutants N140C/F264W and N140C/W806F. Sequencing is respectively performed to confirm whether a coding gene of the β-galactosidase double mutants is correct; Snab1 and Not1 double-enzyme digestion is performed on the plasmid with a correct sequencing result and the pPIC9k vector, enzyme digestion products are connected by a T4 ligase, a connection product is transformed into an *Escherichia coli* JM109 competent cell, bacterium picking is performed to extract the correct plasmid, and the plasmid is transformed into a yeast KM71 cell to obtain recombinant bacteria AorE-M/pPIC9k-N140C/F264W and AorE-M/pPIC9k-N140C/W806F capable of expressing the double mutant genes.

Example 3

Preparation of Wild Bacterium and Mutant β-Galactosidase Solutions

The recombinant bacteria AorE-M/pPIC9k/KM71, AorE-M/pPIC9k-N140C, AorE-M/pPIC9k-F264W, AorE-M/pPIC9k-F3040, AorE-M/pPIC9k-W806F, AorE-M/pPIC9k-N140C/F264W and AorE-M/pPIC9k-N140C/W806F are respectively transferred into the BMGY liquid culture medium, and are cultured at 30° C. for 24 h to obtain a bacteria solution. The bacteria solution is centrifuged, all thalli are transferred into 50 mL of the BMMY liquid culture medium, and cultured at 30° C. for 5 days, wherein methanol of which the final concentration is 0.75% is added every 24 h to perform induced enzyme production. A fermentation solution is centrifuged, and supernate is a crude enzyme solution.

After the enzyme activity of the crude enzyme solution is measured, ONPG hydrolase activities of the wild type β-galactosidase (WT) and the mutant are listed in Table 1.

TABLE 1

Enzyme activities of wild type β-galactosidase and mutant enzymes

| Enzyme | Enzyme Activity (U/mL) |
| --- | --- |
| WT | 185.3 |
| N140C | 9.7 |
| F264W | 23.2 |
| F304Q | 37.5 |
| W806F | 161.2 |
| N140C/F264W | 19.3 |
| N140C/W806F | 32.1 |

It can be seen from Table 1 that the mutants have lower oNPG hydrolase activity than the wild type. In this experiment, the enzyme activity and the yield are not directly proportional, and the level of the hydrolase activity does not represent the level of the yield. The hydrolase activity is only used as a quantitative measure of the amount of enzyme added.

Example 4

Optimum Temperature for Producing Galactooligosaccharide by Transforming Lactose by Using Mutant Enzyme A 60% (W/V) lactose solution is prepared as a substrate, 60 g of lactose is dissolved in 50 mL of pH 4.5 50 mml/L acetic acid buffer, and the volume of the solution is made up to 100 mL. Certain amounts of the wild enzyme and the double-mutant enzyme solution are added, so that the final enzyme activity of the enzyme solution is 2.5 U/mL; the enzyme solution is subjected to reaction at different temperatures, wherein the reaction for the wild type is performed for 10 h, the reaction for the mutant is performed for 5 h, and the reaction time is determined by the pre-experiment; and the galactooligosaccharide yield is analyzed.

Figure 1:
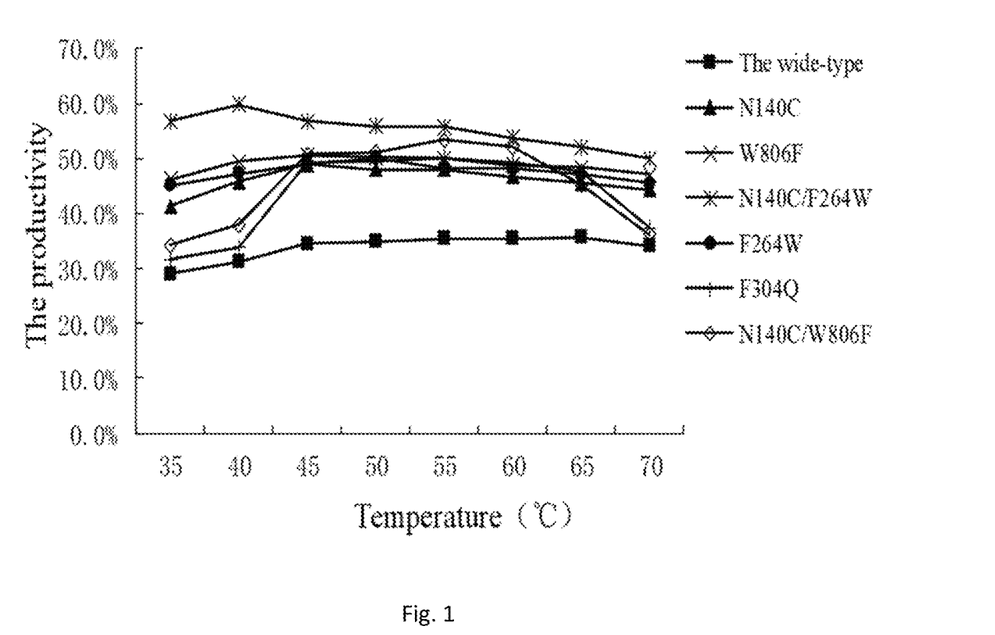
FIG. 1 is optimum temperature for producing galactooligosaccharide by transforming lactose by using a wild enzyme and a mutant.

It can be seen from FIG. 1 that the optimum enzymatic transformation temperature for the wild-type β-galactosidase is 60° C., the optimum enzymatic transformation temperature for the mutants is 40-60° C., and the maximum yield of the wild enzyme is 35.7% while the maximum yield of different mutants is 47.7% to 59.8%, which is greatly improved as compared with the wild enzyme. The maximum yield of the N140C/F264W double-mutant reach 59.8%, which is about 1.67 times that of the wild enzyme. In addition, as can be seen from the accompanying drawing, the temperature has little effect on the wild enzyme and the mutants at 40-60° C., so the present invention is more suitable for industrialized application.

Example 5

Optimum pH for Producing Galactooligosaccharide by Transforming Lactose by Using Mutant Enzyme A 60% (W/V) lactose solution is prepared as a substrate, 60 g of lactose is dissolved in 50 mL of 50 mml/L acetic acid buffers with different pH, and each solution is made up to 100 mL. Certain amounts of the wild enzyme and the double-mutant enzyme solution are added, so that the final enzyme activity of the enzyme solution is 2.5 U/mL. The reaction temperature of the wild type is 60° C., and the reaction temperature of the mutants is determined according to the optimum temperature in the Example 4, ranging from 40 to 60° C. The reaction for the wild type is performed for 10 h, and the reaction for the mutants is performed for 5 h, wherein the reaction time is determined by the pre-experiment; and the galactooligosaccharide yield is analyzed.

Figure 2:
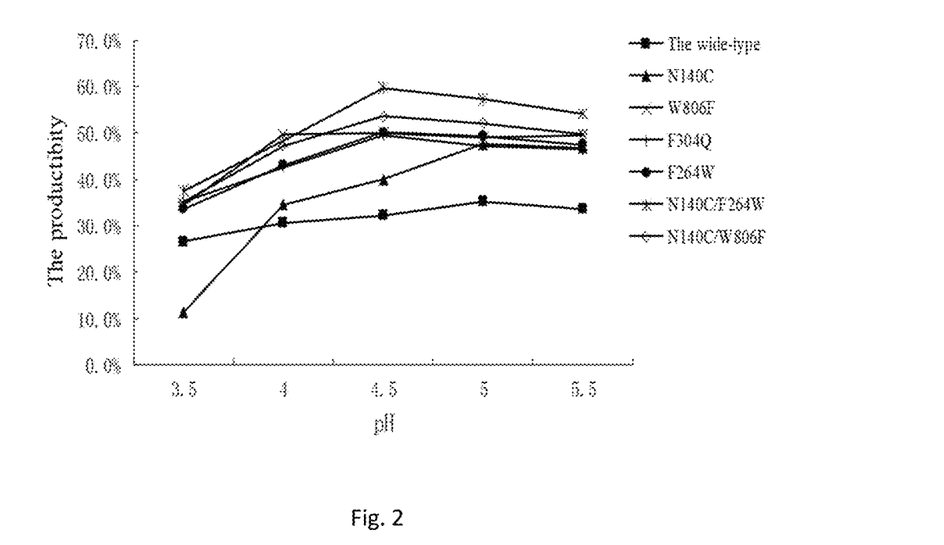
FIG. 2 is optimum pH for producing galactooligosaccharide by transforming lactose by using the wild type and the mutant.

It can be seen from FIG. 2 that except that the optimum pH of N140C is 5, the optimum pH of other mutants is 4.5. The maximum yield of the wild-type enzyme reaches 35.7% while the maximum yield of different mutants is 47.7%-59.8%, which is greatly improved as compared with controls. The maximum yield of N140C/F264W double-mutant reaches 59.8%, which is about 1.67 times that of the wild enzyme.

What is claimed is:

1. A mutant β-galactosidase enzyme comprising a variant of the amino acid sequence of SEQ ID NO: 2 with one or more mutations selected from N140C, F264W, F304Q, and W806F; wherein the enzyme catalyzes conversion of lactose to galactooligosaccharide (GOS).

2. The enzyme according to claim 1, wherein the one or more mutations consist of:
   a) both N140C and F264W, or
   b) both N140C and W806F.

3. A method for preparing galactooligosaccharide (GOS), comprising:
   incubating the enzyme of claim 1 in a solution with lactose at a concentration of 400 g/L to 600 g/L in an acetic acid-sodium acetate buffer, at a pH of 4.5 to 5; and
   shaking the solution in a water bath at a temperature of 40° C. to 60° C. for 5 to 36 hours.

4. The method according to claim 3, wherein 2.5 to 5 U/mL of enzyme is incubated in the solution with the lactose.

5. The enzyme of claim 1, wherein the yield of GOS from lactose catalyzed by the enzyme is increased from 35.2% to 59.8% as compared to wild type enzyme incubated under identical conditions, wherein the wild type enzyme comprises the amino acid sequence of SEQ ID NO: 2 comprising no mutations.

6. The enzyme of claim 3, wherein the yield of GOS from lactose catalyzed by the enzyme is increase from 35.2% to 59.8% as compared to wild type enzyme incubated under identical conditions, wherein the wild type enzyme comprises the amino acid sequence of SEQ ID NO: 2 comprising no mutations.

* * * * *